United States Patent [19]

Smith

[11] 4,034,112
[45] July 5, 1977

[54] ETHANOLAMINE DERIVATIVES HAVING β-ADRENERGIC BLOCKING ACTIVITY

[75] Inventor: Leslie Harold Smith, Macclesfield, England

[73] Assignee: Imperial Chemical Industries Limited, London, England

[22] Filed: Dec. 29, 1975

[21] Appl. No.: 645,300

Related U.S. Application Data

[62] Division of Ser. No. 479,174, June 13, 1974, Pat. No. 3,944,611.

[30] Foreign Application Priority Data

June 22, 1973 United Kingdom ............ 29679/73

[52] U.S. Cl. .......................... 424/321; 260/79.3 R; 260/501.1; 260/501.19; 260/501.17; 260/556 R; 260/556 A; 260/556 AR; 260/556 B
[51] Int. Cl.² ........................................ A61K 31/18
[58] Field of Search .... 260/556 A, 556 AR, 556 B; 424/330, 321

[56] References Cited

UNITED STATES PATENTS

| | | | |
|---|---|---|---|
| 3,816,516 | 6/1974 | Cox et al. | 260/501.17 |
| 3,928,412 | 12/1975 | Smith | 260/465 D |
| 3,944,611 | 3/1976 | Smith | 260/562 R |

*Primary Examiner*—Leonard Schenkman
*Attorney, Agent, or Firm*—Cushman, Darby & Cushman

[57] ABSTRACT

Novel 1-aryl-2-amidoalkylaminoethanol derivatives, processes for their manufacture, pharmaceutical compositions containing them and methods of using them in the treatment of heart diseases. The compounds possess β-adrenergic blocking activity. Representative of the compounds disclosed is 1-phenyl-2-(1,1-dimethyl-2-phenylacetamidoethyl)aminoethanol.

11 Claims, No Drawings

ETHANOLAMINE DERIVATIVES HAVING β-ADRENERGIC BLOCKING ACTIVITY

This is a division of application Ser. No. 479,174, filed June 13, 1974, now U.S. Pat. No. 3,944,611.

This invention relates to a new ethanolamine derivatives which possess β-adrenergic blocking activity.

According to the invention there is provided a new ethanolamine derivative of the formula:

wherein A stands for an alkylene radical of from 2 to 6 carbon atoms, wherein $R^1$ stands for the hydrogen atom or for an alkyl, alkenyl, halogenoalkyl or cycloalkyl radical each of up to 6 carbon atoms, or for an aryl radical of the formula:

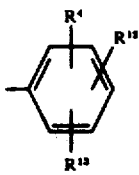

wherein $R^2$, $R^3$, $R^{12}$ and $R^{13}$, which may be the same or different, each stands for a hydrogen or halogen atom, a nitro, amino or cyano radical or an alkyl, alkenyl, alkoxy, alkenyloxy, hydroxyalkyl, alkanoyl, acylamino or alkanesulphonamide radical each of up to 6 carbon atoms, wherein $R^4$ stands for the hydrogen atom or for the hydroxy or carbamoyl radical, wherein $R^5$ stands for the hydrogen atom or for an alkyl radical of up to 6 carbon atoms, wherein X stands for the carbonyl or sulphonyl radical and wherein Y stands for a direct link, or for an alkylene or alkyleneoxy radical each of up to 6 carbon atoms, or for the imino (–NH–) radical, or (except when $R^1$ stands for the hydrogen atom) for the oxygen atom; or an acid-addition salt thereof.

It will be observed that the ethanolamine derivative of the invention possesses an asymmetric carbon atom, namely the carbon atom of the —CHOH— group in the ethanolamine side-chain, and it can therefore exist in racemic and optically-active forms. It is to be understood that this invention encompasses the racemic form of the ethanolamine derivative and any optically-active form which possesses β-adrenergic blocking activity, it being a matter of common general knowledge how a racemic compound may be resolved into its optically-active forms and how the β-adrenergic blocking activity of these forms may be determined. It is to be understood that β-adrenergic blocking activity usually predominates in that optically-active form which has the R absolute configuration of the said —CHOH— group.

A suitable value for the alkylene radical A is, for example, the ethylene, trimethylene, tetramethylene, hexamethylene, 1-methylene, 2-methylethylene or 1,1-dimethylethylene radical. A is preferably the ethylene, 1-methylethylene or 1,1-dimethylethylene radical.

A suitable value for $R^1$ when it stands for an alkyl, alkenyl, halogenoalkyl or cycloalkyl radical is, for example, the methyl, ethyl, n-propyl, isopropyl, n-butyl, isobutyl, t-butyl, n-pentyl, allyl, trifluoromethyl, cyclopropyl, cyclopentyl or cyclohexyl radical.

A suitable value for $R^2$, $R^3$, $R^{12}$ or $R^{13}$ when it stands for a halogen atom is, for example, the fluorine, chlorine, bromine or iodine atom.

A suitable value for $R^2$, $R^3$, $R^{12}$ or $R^{13}$ when it stands for an alkyl, alkenyl, alkoxy, alkenyloxy, hydroxyalkyl, alkanoyl, acylamino or alkanesulphonamido radical is, for example, the methyl, ethyl, n-propyl, allyl, methoxy, isopropoxy, allyloxy, hydroxymethyl, 1-hydroxymethyl, formyl, acetyl, acetamido or methanesulphonamido radical.

A suitable value for $R^5$ when it stands for an alkyl radical is, for example, the methyl or ethyl radical.

A suitable value for Y when it stands for an alkylene or alkyleneoxy radical is, for example, the methylene, ethylene, methyleneoxy, ethyleneoxy, trimethyleneoxy or ethylideneoxy radical.

A suitable acid-addition salt of an ethanolamine deriviative of the invention is, for example, a salt derived from an inorganic acid, for example, a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3-naphthoate), or a salt derived from an acidic synthetic resin, for example, a sulphonated polystyrene resin.

One preferred ethanolamine derivative of the invention is a compound of the formula given above wherein A stands for the ethylene, 1-methylethylene or 1,1-methylethylene radical, wherein $R^1$ stands for an alkyl or cycloalkyl radical each of up to 6 carbon atoms, wherein $R^2$ and $R^3$ both stand for hydrogen, wherein X stands for the carbonyl radical and wherein Y stands for the direct link, or an acid-addition salt thereof.

A second preferred ethanolamine derivative of the invention is a compound of the formula given above wherein A stands for the ethylene, 1-methylethylene or 1,1-dimethylethylene radical, wherein $R^1$ stands for a phenyl, chlorophenyl or methoxyphenyl radical, wherein $R^2$ and $R^3$ both stand for hydrogen, wherein X stands for the carbonyl radical and wherein Y stands for the methylene radical, or an acid-addition salt thereof.

Specific ethanolamine derivatives of the invention are those hereinafter described in the Examples. Of these, preferred compounds by virtue of their high β-adrenergic blocking activity are 1-phenyl-2-(β-cyclopentanecarbonamidoethyl)aminoethanol; 1-phenyl-2-(β-isobutyramidoethyl)aminoethanol; 1-phenyl-2-(β-p-methoxyphenylacetamidoethyl)aminoethanol; 1-phenyl-2-(β-propionamidoethyl)aminoethanol; 1-phenyl-2-(β-n-butyramidoethyl)aminoethanol; 1-phenyl-2-(β-phenylacetamidoethyl)aminoethanol; 1-phenyl-2-(1-methyl-2-p-chlorophenylacetamidoethyl)aminoethanol; 1-phenyl-2-(1-methyl-2-phenylacetamidoethyl)aminoethanol; 1-phenyl-2-(1,1-dimethyl-2-isobutyramidoethyl)aminoethanol and 1-phenyl-2-(1,1-dimethyl-2-phenylacetamidoethyl)aminoethanol and the acid-addition salts thereof; and of these the most preferred compounds are 1-phenyl-2-(1-methyl-2-phenylacetamidoethyl)aminoethanol, particularly the isomers (1R)-1-phenyl-2-[(1R)-1-methyl-2-phenylacetamidoethyl]aminoethanol and (1R)-1-phenyl-2-[(1S)-1-methyl-2-phenylacetamidoethyl- ]aminoethanol, thereof, and the acid-addition salts thereof.

The ethanolamine derivative of the invention may be manufactured by any chemical process known to be useful for the manufacture of chemically-analogous compounds.

According to a further feature of the invention there is provided a process for the manufacture of the ethanolamine derivative of the invention which comprises assembling in sequence, by chemical synthesis, the four radicals:

i. a 1-hydroxy-1-phenylethyl radical of the formula:

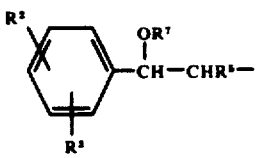

wherein $R^2$, $R^3$ and $R^5$ have the meanings stated above and wherein $R^7$ stands for hydrogen or for a protecting group;

ii. an imino radical of the formula $-NR^8-$, wherein $R^8$ stands for hydrogen of for a protecting group;

iii. a radical of the formula $-A-NR^9-$ wherein A has the meaning stated above and wherein $R^9$ stands for hydrogen or for a protecting group; and iv. a radical of formula $-X-Y-R^1$ wherein $R^1$, X and Y have the meanings stated above;

whereafter if one or more of $R^7$, $R^8$ and $R^9$ stands for a protecting group, the one or more protecting groups are removed.

The various stages of the assembly may be carried out in any possible order. Thus, for example:

a. A phenylalkyl derivative of the formula:

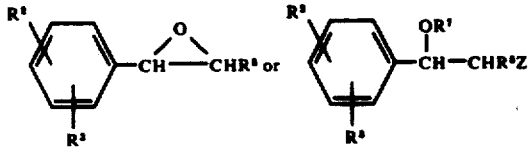

wherein $R^2$, $R^3$, $R^5$ and $R^7$ have the meanings stated above and wherein Z stands for a displaceable radical, or a mixture of such compounds, may be reacted with an amine of the formula:

$HNR^8-A-NR^9-X-Y-R^1$ wherein A, $R^1$, $R^8$, $R^9$, X and Y have the meanings stated above, or with a precursor of such an amine.

A suitable value for Z is, for example, a halogen atom, for example the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical.

The reaction may be carried out at ambient temperature or it may be accelerated or completed by the application of heat, for example by heating to a temperature of 90°-110°C.; it may be carried out at atmospheric or at an elevated pressure, for example by heating in a sealed vessel; and it may be carried out in an inert diluent or solvent, for example an alcohol, for example methanol, ethanol, n-propanol or isopropanol or an excess of the amine may be used as diluent or solvent.

Either phenylalkyl derivative used as starting material, or a mixture thereof, may be obtained by the reduction, for example by means of sodium borohydride or aluminium isopropoxide, of a compound of the formula:

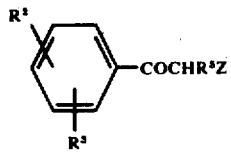

wherein $R^2$, $R^3$, $R^5$ and Z have the meanings stated above. This compound in turn may be obtained from the corresponding acetophenone derivative either directly, when Z stands for a halogen atom, or via the corresponding hydroxy compound of the formula:

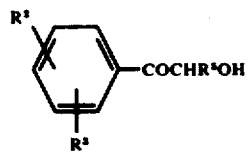

wherein $R^2$, $R^3$ and $R^5$ have the meanings stated above.

b. A compound of the formula:

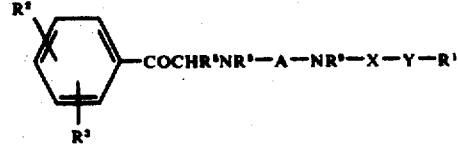

wherein A, $R^1$, $R^2$, $R^3$, $R^5$, $R^8$, $R^9$, X and Y have the meanings stated above, may be reduced.

The reduction may be carried out by means of a metal borohydride, for example sodium borohydride, in an appropriate diluent or solvent, for example methanol, or by means of catalytic hydrogenation, for example hydrogen in the presence of a palladium, platinum or nickel catalyst.

The starting material may be obtained by the reaction of a compound of the formula:

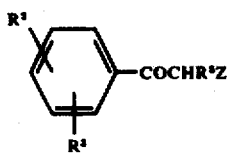

wherein $R^2$, $R^3$, $R^5$ and Z have the meanings stated above, with an amine of the formula:

$HNR^8-A-NR^9-X-Y-R^1$ wherein A, $R^1$, $R^8$, $R^9$, X and Y have the meanings stated above, or with a precursor of such an amine, in an appropriate solvent, for example dioxan or methanol.

c. A compound of the formula:

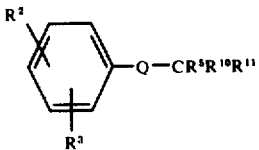

wherein $R^2$, $R^3$ and $R^5$ have the meanings stated above, wherein Q stands for the carbonyl (—CO—) radical or for a radical of the formula

wherein $R^7$ has the meaning stated above, and wherein either $R^{10}$ and $R^{11}$ together form the oxo (=O) radical, or wherein $R^{10}$ and $R^{11}$, which may be the same or different, each stands for the hydroxy radical or for an alkoxy radical of up to 6 carbon atoms, may be reacted with an amine of the formula:

$$HNR^1-A-NR^9-X-Y-R^1$$

wherein A, $R^1$, $R^8$, $R^9$, X and Y have the meanings stated above, under reducing conditions.

Suitable reducing conditions are provided by, for example, an alkali metal borohydride, for example sodium borohydride, in an appropriate diluent or solvent, for example methanol or ethanol, or by, for example, hydrogen in the presence of a catalyst, for example a platinum, palladium or nickel catalyst.

The starting material wherein Q stands for the carbonyl radical may be obtained by the oxidation of an acetophenone derivative of the formula:

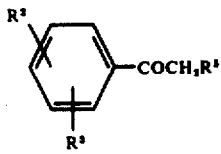

wherein $R^2$, $R^3$ and $R^5$ have the meanings stated above, with selenium dioxide in an appropriate solvent, for example aqueous dioxan, optionally followed by acetal or hemiacetal formation. The starting material wherein Q stands for a radical of the formula —CHOH— may be obtained by the reduction of the acetal of the corresponding compound wherein Q stands for the carbonyl radical.

d. The series of reaction described under (a) or (b) or (c) above may be carried out except that an amine of the formula $R^8NH_2$ is used in place of an amine of the formula:

$$HNR^1-A-NR^9-X-Y-R^1$$

it being understood that when $R^8$ stands for hydrogen the amine is ammonia. The final product obtained, which has the formula:

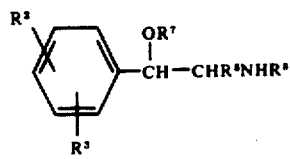

wherein $R^2$, $R^3$, $R^5$, $R^7$ and $R^8$ have the meanings stated above, may alternatively be obtained, when $R^8$ stands for hydrogen, by the reduction of, for example, a compound of the formula:

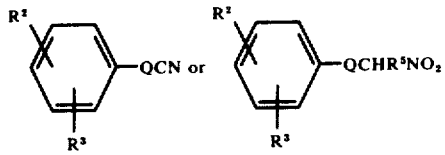

wherein $R^2$, $R^3$, $R^5$ and Q have the meanings stated above (which compound may be obtained, when Q stands for the —CHOH— radical, by the reaction of a corresponding benzaldehyde derivative with respectively, hydrogen cyanide or a nitroalkane, for example nitromethane), or by the reduction of an oxime of the formula:

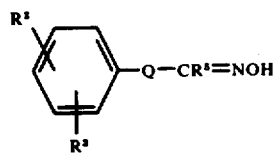

wherein $R^2$, $R^3$, $R^5$ and Q have the meanings stated above (which oxime may be obtained by conventional means from the corresponding aldehyde or ketone, or by the reduction of any other suitable compound which contains a group reducible to a primary amino group, for example a diazo or azido group.

The radical $—A—NR^9—X—Y—R^1$ may then be inserted as a separate step, for example either by the reaction of the above final product with a compound of the formula:

$$Z-A-NR^9-X-Y-R^1$$

wherein A, $R^1$, $R^9$, X, Y and Z have the meanings stated above, or, by the reaction under reducing conditions of the same final product with a carbonyl compound of the formula:

$$A^1-CO-A^2-NR^9-X-Y-R^1$$

wherein $R^1$, $R^9$, X and Y have the meanings stated above and wherein $A^1$ stands for hydrogen or for an alkyl radical and $A^2$ stands for an alkylene radical such that the radical

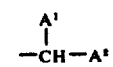

has the same meaning as is stated above for A.

The reaction involving a compound of the formula:

$$Z-A-NR^9-X-Y-R^1$$

may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenation catalyst, for example palladium or platinum, in an inert diluent or solvent, for example in one or move solvents selected from water, ethanol and an excess of the carbonyl compound used as starting material; or by the presence of an alkali metal borohydride, for example sodium borohydride or lithium cyanoborohydride, in an inert diluent or solvent, for example in one or more solvents selected from water, ethanol, methanol and an excess of the carbonyl compound used as starting material. It is to be understood that when in the starting material $R^1$ stands for an alkenyl radical, or one or both of $R^2$ and $R^3$ stands for a halogen atom or for a nitro, cyano, alkenyl, alkenyloxy or alkanoyl radical, hydrogen and a hydrogenation catalyst are preferably not used to provide the reducing conditions, in order to prevent the radical $R^1$, $R^2$ or $R^3$ from being affected by catalytic hydrogenation.

e. The series of reactions described under (a), (b), (c) or (d) above may be carried out except that an amine containing a radical of the formula:

wherein A, $R^8$ and $R^9$ have the meanings stated above, is used in place of an amine of the formula:

or the reaction described under (d) above may be carried out except that the radical —A—NHR$^9$ is inserted in place of the radical —A—NR$^8$—X—Y—R$^1$. The amidic linkage —NR$^8$—X— may then be formed as a separate step by reaction of the resulting product, which has the formula:

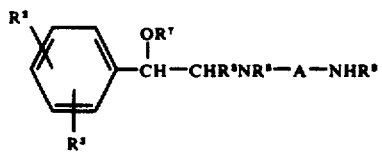

wherein $R^2$, $R^3$, $R^5$, $R^7$, $R^8$, $R^9$ and A have the meanings stated above, with a compound of the formula:

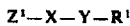

wherein $R^1$, X and Y have the meanings stated above and wherein $Z^1$ stands for a displaceable radical, or, when X stands for the carbonyl radical and Y stands for the imino radical, with an isocyanate of the formula OCN—R$^1$, wherein R$^1$ has the meaning stated above.

The displaceable radical $Z^1$ may be a halogen atom, for example the chlorine or bromine atom, or an alkoxy radical, for example the methoxy or ethoxy radical, or it may be the oxygen atom such that the compound (R$^1$—Y—X)$_2$Z$^1$ is an acid anhydride.

The reaction to form the amide linkage may be carried out in an inert diluent or solvent, for example toluene or tetrahydrofuran.

The intermediate product of the formula:

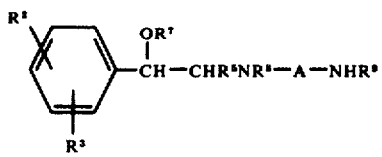

may, when R$^9$ stands for hydrogen, alternatively be obtained by, for example, the reduction of the nitro, cyano or carbamoyl radical of a compound of the formula:

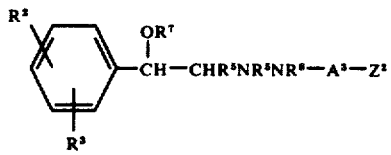

wherein $R^2$, $R^3$, $R^5$, $R^7$ and $R^8$ have the meanings stated above, wherein A$^3$ stands for an alkylene radical such that —A$^3$—CH$_2$ has the same meaning as is stated above for A and wherein $Z^2$ stands for the —CH$_2$NO$_2$, —CN or —CONH$_2$ radical.

f. A compound wherein one or more of $R^7$, $R^8$ and $R^9$ stands for a protecting group may be prepared by the series of reactions described under (a), (b), (c), (d) or (e) above. Alternatively, a suitable protecting group may be introduced by conventional means into an intermediate compound at any stage preceding the final stage.

A suitable value for $R^7$ when it stands for a protecting group is, for example, a hydrogenolysable radical, for example an α-arylalkyl, α-arylalkoxycarbonyl or α-arylalkoxymethyl radical, for example the benzyl, benzyloxycarbonyl or benzyloxymethyl radical, or an acyl radical, for example an alkanoyl radical of up to 20 carbon atoms, for example the acetyl, t-butoxycarbonyl or 2,2,2-trichloroethoxycarbonyl radical, or an aroyl radical of up to 10 carbon atoms, for example the benzoyl radical, or an α-alkoxyalkyl radical (that is, a radical which forms with the adjacent oxygen atom an acetal radical), for example the tetrahydropyranyl radical, or a tertiary alkyl radical, for example the t-butyl radical.

A suitable value for $R^8$ when it stands for a protecting group is, for example, a hydrogenolysable or tertiary alkyl radical as defined for $R^7$, or a relatively easily hydrolysable acyl radical, for example the 2,2,2-trichloroethoxycarbonyl or t-butoxycarbonyl radical. It is to be understood that when R$^8$ stands for an acyl radical, this radical must be removable under conditions which will not destroy the amidic linkage —NH—X—.

Alternatively, $R^7$ and $R^8$ may be joined together so that one protecting group serves to protect both the oxygen and nitrogen atoms. Such protecting group may be, for example, a radical of the formula —CHR$^6$—, wherein R$^6$ stands for hydrogen, or for an alkyl radical of up to 4 carbon atoms or an aryl radical of up to 10 carbon atoms, such that it forms, together with the adjacent oxygen and nitrogen atoms and the two adjacent carbon atoms an oxazolidine nucleus.

A suitable value for $R^9$ when it stands for a protecting group is, for example, a hydrogenolysable or tertiary alkyl group as defined for $R^7$ or $R^8$.

The hydrogenolysable protecting group $R^7$, $R^8$ or $R^9$ may be removed, for example, by catalytic hydrogenation, for example by hydrogenation in the presence of a palladium-oncharcoal catalyst, in an inert diluent or solvent, for example ethanol or aqueous ethanol. The process may be accelerated or completed by the presence of an acidic catalyst, for example hydrochloric or oxalic acid.

The acyl protecting group $R^7$ or $R^8$ may be removed by hydrolysis in the presence of a base, for example an alkali metal hydroxide, in a diluent or solvent, for example water, methanol, ethanol or a mixture thereof. It is to be understood that the hydrolytic conditions used must be sufficiently mild to avoid hydrolysis of the amidic linkage —NH—X—.

The α-alkoxyalkyl protecting group $R^7$ or the protecting group $R^8CH$- formed by $R^7$ and $R^8$ taken together may be removed by hydrolysis in the presence of an acid, for example a mineral acid, for example aqueous hydrochloric acid, and the hydrolysis may be carried out at a temperature of up to 100° C.

The tertiary alkyl protecting group $R^7$, $R^8$ or $R^9$, or the acyl protecting group $R^7$, $R^8$ or $R^9$ when it stands for a tertiary alkoxycarbonyl radical, for example the t-butoxycarbonyl radical, may be removed by treatment with an acid, for example hydrogen chloride, in anhydrous conditions, for example in ethereal solution.

It is to be understood that a compound wherein the substituent $R^2$, $R^3$, $R^{12}$ or $R^{13}$ is a reactive radical may be converted into a different compound wherein $R^2$, $R^3$, $R^{12}$ or $R^{13}$ is a different substituent. Thus, for example, a compound wherein one or more of $R^2$, $R^3$, $R^{12}$ and $R^{13}$ stands for a nitro, alkenyl, alkenyloxy or alkanoyl radical may be reduced to the corresponding compound wherein one or more of $R^2$, $R^3$, $R^{12}$ and $R^{13}$ stands for, respectively, an amino, alkyl, alkoxy or hydroxyalkyl radical.

It is further to be understood that a compound wherein $R^4$ stands for the hydroxy radical may be obtained by the hydrogenolysis of the corresponding compound wherein $R^4$ stands for an α-arylalkoxy radical, for example the benzyloxyradical.

One preferred process for the manufacture of the ethanolamine derivative of the invention comprises the reaction of a compound of the formula:

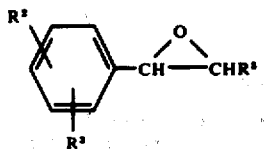

wherein $R^2$, $R^3$ and $R^5$ have the meanings stated above, with an amine of the formula:

wherein A, $R^1$, X and Y have the meanings stated above.

A second, and more particularly preferred, process for the manufacture of the ethanolamine derivative of the invention comprises the reaction of a compound of the formula:

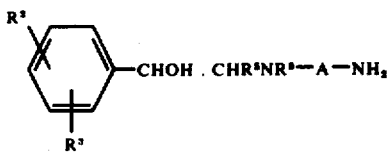

wherein $R^2$, $R^3$, $R^5$, $R^6$ and A have the meanings stated above, with a compund of the formula:

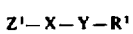

wherein $R^1$, X, Y and $Z^1$ have the meanings stated above. Preferably in this reaction $R^8$ is the hydrogen atom or the benzyl radical, and $Z^1$ is a halogen atom, an alkoxy radical, for example the methoxy or ethoxy radical, or the oxygen atom of an anhydride group.

Optically-active forms of the ethanolamine derivative of the invention may be obtained by the resolution by conventional means of the corresponding racemic ethanolamine derivative of the invention.

The said resolution may be carried out by reacting the racemic ethanolamine derivative with an optically-active acid, followed by fractional crystallisation of the diastereoisomeric mixture of salts thus obtained from a diluent or solvent, for example ethanol, whereafter the optically-active ethanolamine derivative is liberated from the salt by treatment with a base. A suitable optically-active acid is, for example, (+)- or (−)-0,0-di-p-toluoyltartaric acid.

The resolution process may be facilitated by treating the partially resolved ethanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

Alternatively, an optically-active form of an ethanolamine derivative may be obtained by carrying out a process for the manufacture of the ethanolamine derivative using an appropriate optically-active starting material. This procedure is particularly preferred when, apart from the —CHOH— asymmetric centre, there is a further asymmetric centre in the alkylene radical —A— or in the group —Y—$R^1$, and it is a particularly appropriate procedure when used in the series of reactions described under (e) above.

An optically-active intermediate of the formula:

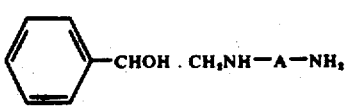

may conveniently be obtained by the reaction of mandelic acid of the formula:

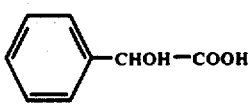

which is commerically-available in both (R)-(-)- and (S) -(+) forms, with an amino-acid amide of the formula:

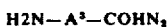

wherein $A^3$ has the meaning stated above, followed by the reduction with borane of the two carbonyl radicals in the product thus obtained, which has the formula:

In particular, the compounds of the above formulae in which the —CHOH— group has the (R)— configuration are valuable intermediates.

According to a further feature of the invention, there is provided a novel chemical intermediate of the formula:

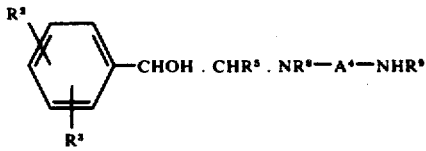

wherein $R^2$, $R^3$, $R^5$, $R^6$ and $R^8$ have the meanings stated above and wherein $A^4$ stands for the 1-methylethylene

radical, or an acid-addition salt thereof.

A particularly preferred novel chemical intermediate has the formula given above wherein $R^2$, $R^3$, $R^5$ and $R^6$ all stand for hydrogen atoms and wherein $R^8$ stands for the hydrogen atom or for the benzyl radical, and a most particularly preferred compound of this type has the (R)— configuration of the —CHOH— group.

The ethanolamine derivative of the invention in free base form may be converted into an acid-addition salt thereof by reaction with an acid by conventional means.

As stated above, the ethanolamine derivative of the invention or an acid-addition salt thereof possesses β-adrenergic blocking activity, and in some of the ethanolamine derivatives this activity is cardio-selective. The β-adrenergic blocking activity may be determined by the reversal of isoprenaline-induced tachycardia in rats or cats, a standard test for the determination of β-adrenergic blocking activity, and the cardio-selectivity may be determined by the relative freedom from antagonism of isoprenaline-induced vasodilatation in cats or of the relief produced by isoprenaline of histamine-induced bronchospasm in guinea-pigs.

A preferred ethanolamine derivative of the invention if 5 to 20 times more active as a β-adrenergic blocking agent than practolol. At doses of an ethanolamine derivative of the invention which produce effective β-adrenergic blockade in rats or cats, no symptoms of toxicity are apparent.

Some of the ethanolamine derivatives of the invention, and in particular the compound 1-phenyl-2-(1-methyl-2-phenyl-acetamidoethyl) aminoethanol and especially the highly active stereoisomers thereof, possess partial β-adrenoceptor agonist activity as well as the ability to block the action of exogenous and endogenous β-adrenergic stimulants. This secondary activity is in some cases sufficiently marked for the ethanolamine derivative to be useful for the relief of bronchospasm and for the dilatation of blood vessels with concomitant lowering blood pressure.

The ethanolamine derivative of the invention may be administered to warm-blooded animals, including man, in the form of a pharmaceutical composition comprising as active ingredient at least one ethanolamine derivative of the invention, or an acid-addition salt thereof, in association with a pharmaceutically-acceptable diluent or carrier thereof.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the ethanolamine derivative of the invention, one or more drugs selected from sedatives, for example phenobarbitone, meprobamate, chlorpromazine and the benzodiazepine sedative drugs, for example chlordiazepoxide and diazepam: vasodilators, for example glyceryl trinitrate, pentaerythritol tetanitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; α-adrenergic blocking agents, for example phentolamine and sympathomimetic bronchodilators, for example isoprenaline, orciprenaline, adrenaline and ephedrine When used for the treatment of heart diseases, for example angina pectoris and cardiac arrhythmias, or for the treatment of bronchospasm, hypertension or anxiety states in man, it is expected that the ethanolamine derivative would be given to man at a total oral dose of between 20 mg. and 600 mg. daily, at doses spaced at 6–8 hourly intervals, or at an intravenous dose of between 1 mg. and 20 mg. Preferred oral dosage forms are tablets or capsules containing between 10 and 100 mg., and preferably 10 mg. or 40 mg. of active ingredient. Preferred intravenous dosage forms are sterile aqueous solutions of the ethanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of 2.24 g. of N-(β-aminoethyl) benzenesulphonamide hydrochloride, 1.2 ml. of styrene oxide, 50 ml. of isopropanol, 0.4 g. of sodium hydroxide and 5 ml. of water is heated under reflux for 5 hours. The mixture is evaporated to dryness under reduced pressure and the residue is dissolved in 20 ml. of ethyl acetate. This solution is added to a solution of 1.26 g. of oxalic acid in 20 ml. of ethyl acetate. The mixture is filtered and the solid residue is crystallised from ethanol. There is thus obtained 2-(β-benzenesulphonamido-ethylamino) -1-phenylethanol hydrogen oxalate, m.p. 228°–230° C. (with decomposition).

EXAMPLE 2

A mixture of 2.32 g. of N-(β-aminoethyl) cyclopentane-carboxamide oxalate, 1.2 ml. of styrene oxide, 50 ml. of isopropranol, 0.8 g. of sodium hydroxide and 4 ml. of water is heated under flux for 4 hours. The mixture is filtered, the filtrate is evaporated to dryness under reduced pressure and the residue is crystallised from ethyl acetate. There is thus obtained 2-(β-cyclopentanecarbonamidoethylamino)- 1-phenylethanol, m.p. 106°–108° C.

The process described above is repeated except that the appropriate N-(β-aminoethyl) amide is used as starting material in place of N-(β-aminoethyl) cyclopentanecarboxamide. There are thus obtained the compounds described in the following table, all of which are crystallised from ethyl acetate:

| R | m.p.(° C.) |
| --- | --- |
| methyl | 106–108 |
| isopropyl | 100–101 |
| n-butylamino | 102–104 |
| p-methoxybenzyl | 114–115 |
| p-chlorobenzyl | 117–120 |
| p-chlorophenoxymethyl | 104–106 |

EXAMPLE 3

The process described in Example 2 is repeated except that the appropriate N-(β-aminoethyl) amide is used as starting material in place of N-(β-aminoethyl) cyclopentane-carboxamide. There are thus obtained the compounds described in the following tables:

| R | m.p.(° C.) | crystallisation solvent |
| --- | --- | --- |
| ethyl | 91–92 | ethyl acetate |
| n-pentyl | 87–88 | ethyl acetate |
| cyclohexyl | hydrochloride 217–218 | isopropanol |
| methoxymethyl | 94–96 | ethyl acetate |
| phenyl | 122–124 | ethyl acetate |
| benzyl | 113–114 | ethyl acetate |
| anilino | 125–126 | ethyl acetate |
| allylamino | 102–104 | diethyl ether |
| o-allyloxy-phenoxymethyl | oxalate 137–139 | acetonitrile |
| o-allylphenoxy-methyl | oxalate 164–165 | isopropanol |

| R | m.p.(° C.) | crystallisation solvent |
| --- | --- | --- |
| n-propyl | oxalate 180–182 | ethanol |
| o-nitrophenyl | hydrogen oxalate 208–209 | aqueous ethanol |
| benzyl | 100–102 | ethyl acetate |

EXAMPLE 4

A mixture of 1.92 g. of N-(β-aminopropyl) phenylacetamide, 1.2 ml. of styrene oxide and 40 ml. of isopropanol is heated under reflux for 18 hours and then evaported to dryness under reduced pressure. The residue is dissolved in 25 ml. of ethyl acetate and the solution added to a solution of 1.26 g. of oxalic acid in 25 ml. of ethyl acetate. The mixture is filtered and the solid residue is crystallised from ethanol. There is thus obtained 2-(1-methyl-2-phenylacetamido-ethylamino) -1-phenylethanol hydrogen oxalate, m.p. 160°–161° C.

The process described above is repeated except that the appropriate N-aminoalkylamide is used as starting material in place of N-(β-aminopropyl) phenylacetamide. There are thus obtained the compounds described in the following tables:

| A | R | m.p.(° C.) | crystallisation solvent |
| --- | --- | --- | --- |
| —CH(CH₃)CH₂— | cyclohexyl | oxalate 174–175 | ethyl acetate/ isopropanol |
| —CH(CH₃)CH₂— | o-chlorobenzyl | 130–131 | ethyl acetate |
| —C(CH₃)₂CH₂— | isopropyl | hydrogen oxalate 197–198 | ethanol |
| —C(CH₃)₂CH₂— | benzyl | hydrogen fumarate 159–160 | ethanol |
| —(CH₂)₃— | isopropyl | 108–109 | ethyl acetate |

EXAMPLE 5

A mixture of 4.6 g. of 2-bromo-1-(o-chlorophenyl)-ethanol, 3.6 g. of N-(β-aminoethyl) phenylacetamide and 50 ml. of ethanol is heated at 40° C. for 3 days and then evaporated to dryness. The residue is triturated with 50 ml. of acetonitrile, the mixture is filtered and the filtrate is evaporated to dryness. The residue is stirred with 200 ml. of aqueous 4N-hydrobromic acid and the mixture is extracted 3 times with 50 ml. of ethyl acetate each time. The aqueous acidic phase is basified to pH 12 with aqueous 11N-sodium hydroxide solution and the mixture is extracted 3 times with 50 ml. of ethyl acetate each time. The combined ethyl acetate extracts are dried over magnesium sulphate and evaporated to dryness under reduced pressure. The residue is dissolved in 50 ml. of methanol and the solution is added to a solution of 2.3 g. of fumaric acid in 50 ml. of methanol. The mixture is filtered and the solid residue is triturated with 50 ml. of acetonitrile. The mixture is filtered and the residue is crystallised from isopropanol. There is thus obtained 1-(o-chlorophenyl) -2-(β-phenylacetamidoethylamino) ethanol hydrogen fumarate, m.p. 160°–162° C.

The process described above is repeated except that 4.2 g. of 2-bromo-1-;(3,4-dichlorophenyl) ethanol and 2.2 g. of N-(β-aminoethyl) isobutyramide are used as starting materials. There is thus obtained 1-(3,4-dichlorophenyl)-2-(β-isobutyramido-ethylamino) ethanol hydrochloride, m.p. 194°–196° C. after crystallisation from acetonitrile.

EXAMPLE 6 p-Bromophenacyl bromide (2.5 g.) are added to a mixture of 3.9 g. of N-(βaminoethyl isobutyramide and 50 ml. of methanol which is stirred at 10° C., and the mixture is then stirred for a further 20 minutes. Aqueous 48% hydrobromic acid (1.88 ml.) are added and the mixture is again cooled to 10° C. Sodium borohydride (0.48 g. ) is added and the mixture is stirred for 1½ hours, acidified with aqueous hydrochloric acid and evaporated to dryness under reduced pressure. The residue is stirred with 150 ml. of water and the mixture is extracted 3 times with 50 ml. of ethyl acetate each time. The aqueous phase is basified with 11N-aqueous sodium hydroxide solution and extracted 3 times with 75 ml. of ethyl acetate each time. The combined ethyl acetate extracts are dried over anhydrous magnesium sulphate and evaporated to dryness under reduced pressure, and the residue is crystallised from ethyl acetate. There is thus obtained 2(β-isobutyramido-ethyl) amino-1-p-bromophenylethanol, m.p. 138°-140° C.

The process described above is repeated except that 2.3 g. of p-methoxyphenacyl bromide are used in as starting material. There is thus obtained 2-(β-isobutyramidoethyl)-amino-1-p-methoxyphenylethanol, m.p. 112-113° C.

The process described above is repeated except that p-methylphenacyl bromide and N-(β-aminoethyl) propionamide are used as starting materials. There is thus obtained 2-(β-propionamidoethyl) amino-1-p-tolyethanol, m.p. 106°-107° C. (crystallised from ethyl acetate).

EXAMPLE 7

N-(β-Aminoethyl) phenylacetamide (1.78 g.) are added to a solution of 1.4 ml. of α-bromopropiophenone in 25 ml. of dioxan and the mixture is stirred at laboratory temperature for 90 minutes and then acidified with ethereal hydrochloric acid. The liquid phase is removed by decantation, the residue is stirred with 25 ml. of ethyl acetate and the mixture is filtered. The solid residue is added portionwise to a solution of 1.9 g. of sodium borohydride in 25 ml. of methanol which is maintained at 0°-10° C., and the mixture is stirred for one hour at 10° C. and the acidified with 11N-aqueous hydrochloric acid and filtered. The filtrate is evaporated to dryness under reduced pressure and the residue is crystallised from isopropanol. There is thus obtained threo-2-methyl-(β-phenylacetamidoethylamino)-1-phenylethanol hydrochloride, m.p. 166°-168° C.

EXAMPLE 8

A mixture of 3.30 g. of N-(β-benzylaminoethyl)-isobutyramide, 300 ml. of methanol and 18.2 g. of p-nitro-phenacyl bromide is stirred at 10° C. for 30 minutes. Sodium borohydride (8.5 g.) are then added portionwise and the mixture is stirred at 10° C. for a further 1 hour and then acidified to pH 2 with aqueous 11N-hydrochloric acid. The mixture is filtered and the filtrate is evaporated to dryness under reduced pressure. The residue is stirred with 100 ml. of aqueous 2N-sodium hydroxide solution and 100 ml. of chloroform and the chloroform is phase is separated, dried over anhydrous magnesium sulphate and evaporated to dryness under reduced pressure. The residue is stirred with 300 ml. of ether and the mixture is cooled and filtered. The solid residue is crystallised from a mixture of ethyl acetate and cyclohexane (1:4 v/v) and there is thus obtained 2-(N-benzyl-N-β-isobutyr-amidoethylamino) -1-(4-nitrophenyl) ethanol, m.p. 117°-118° C.

A solution of 2.7 g. of hydrazine hydrate in 20 ml. of ethanol is added dropwise during 30 minutes to a mixture of 7.0 g. of the above material, 100 ml. of ethanol and 2 gm. of Raney Nickel. The mixture is filtered and the filtrate is evaporated to dryness under reduced pressure. There is thus obtained, as an oil which is used without further purification, 1-(4-aminophenyl)-2-(N-benzyl-N-β-isobutyramidoethylamino)-ethanol.

A mixture of 0.8 g. of the above compound, 30 ml. of ethanol and 0.2 g. of a 30% palladium-on-charcoal catalyst is shaken with hydrogen at laboratory temperature and atmospheric pressure until 95 ml. of hydrogen have been absorbed. The mixture is filtered, the filtrate is evaporated to dryness under reduced pressure and the residue is crystallised from acetonitrile. There is thus obtained 1-(4-aminophenyl)-2-(β-isobutyramido-ethylamino) ethanol, m.p. 141°-142° C.

EXAMPLE 9

A mixture of 4.4 g. of N-(β-N-benzylaminoethyl)-isobutyramide, 50 ml. of dioxan and 2.92 g. of p-methane-sulphonamidophenacyl bromide is stirred at ambient temperature for 1 hour, and then filtered, and the filtrate is evaporated to dryness under reduced pressure. The residue is stirred with 50 ml. of water and the mixture is extracted twice with 50 ml. of ethyl acetate each time. The combined ethyl acetate extracts are dried over anhydrous magnesium sulphate and evaporated to dryness under reduced pressure. Sodium borohydride (1.14 g.) are added, portionwise, to a stirred solution of the residue in 30 ml. of ethanol which is maintained at 10° C., and the mixture is stirred for 30 minutes, acidified with aqueous 11N-hydrochloric acid, diluted with 300 ml. of water and neutralised with 10% w/v aqueous sodium bicarbonate solution. The mixture is extracted 3 times with 50 ml. of ethyl acetate each time, and the combined extracts are dried over anhydrous magnesium sulphate and evaporated to dryness under reduced pressure. The residue is triturated with 50 ml. of ether, the mixture is filtered and the solid residue is crystallised from 30 ml. of ethyl acetate. There is thus obtained 2-(N-benzyl-N-β-isobutyramidoethylamino)-1-(p-methane-sulphonamidophenyl) ethanol, m.p. 112°-113° C.

A mixture of 1.73 g. of the above compound, 30 ml. of acetic acid and 0.2 g. of a 30% palladium-on-charcoal catalyst is shaken with hydrogen at laboratory temperature and atmospheric pressure until 125 ml. of hydrogen have been absorbed. The mixture is filtered, the filtrate is evaporated to dryness under reduced pressure, the residue is dissolved in 50 ml. of ethyl acetate and the solution is acidified with ethereal hydrogen chloride solution. The mixture is filtered and the solid residue is crystallised from 25 ml. of ethanol. There is thus obtained 2-(β-isobutyramidoethylamino)-1-(p-methane-sulphonamidophenyl) ethanol hydrochloride, m.p. 183°-184° C.

The various N-aminoaklylamides and N-benzyl-amino-alkylamides used as starting material in Examples 1 to 9 have mostly been described in our co-pending U.K. Pat. Application No. 57970/72 (published as German Offenlegungschrift No. 2,362,568). Those which are novel may be obtained by a similar process to those therein described. The following novel intermediate amides have been characterised:

N-(β-aminopropyl) cyclohexanecarboxamide oxalate, m.p. 188° -190 ° C. (with decomposition);

N-(β-aminoethyl(benzylsulphonamide hydrochloride, m.p. 192°-194° C.

N-(β-aminoethyl)-o-allylphenoxyacetamide oxalate, m.p. 142°-143° C.

EXAMPLE 10

A mixture of 5.76 g. of N-(β-aminopropyl) phenylacetamide, 50 ml. of ethanol and 4.56 g. of phenylglyoxal is stirred at laboratory temperature for 1 hour. Sodium borohydride (1.04 g.) are then added portionwise during 10 minutes and the mixture is stirred for 1 hour, acidified with acetic acid, diluted with 200 ml. of water and shaken with 30 ml. of ether. The aqueous phase is separated, neutralised with solid potassium carbonate and extracted 3 times with 50 ml. of ethyl acetate each time. The combined ethyl acetate extracts are dried over anhydrous magnesium sulphate and evaporated to dryness under reduced pressure. The residue is crystallised from ethanol and there is thus obtained 2-(1-methyl-2-phenyl-acetamidoethylamino)-1-phenylethanol hydrogen oxalate, m.p. 160°–161° C.

EXAMPLE 11

A mixture of 2-amino-1-phenylethanol (0.685 g.), N-(2-oxopropyl) phenylacetamide (0.995 g.), Molecular Sieve Type 4 A (B.D.H.; 2.0 g.) and ethanol 15 ml. is heated under reflux for 2 hours. Further Sieve (10 g.) is added, the mixture is heated under reflux for 18 hours, yet further Sieve (8 g.) is added and mixture is heated under reflux for 20 hours. The mixture is filtered, an excess of sodium borohydride is added and the mixture is stirred for 1 hour and then diluted with water and extracted with ethyl acetate. The ethyl acetate extract is washed with water, dried over magnesium sulphate and evaporated to dryness under reduced pressure. The residue is dissolved in ethanol and an excess of a solution of oxalic acid in ether is added. The mixture is filtered and the solid residue is crystallised from ethanol. There is thus obtained 2-(1-methyl-2-phenylacetamidoethylamino)-1-phenylethanol hydrogen oxalate hemihydrate, m.p. 160° –161° C.

The N-(2-oxopropyl) phenylacetamide used as starting material may be obtained as follows:

Jones' reagent (2.67N chromium trioxide in aqueous sulphuric acid; 230 ml.) is added during 30 minutes to a stirred solution of 1-phenylacetamidopropan-2-ol(146.7 g.) in chloroform (750 ml.) which is maintained below 20° C. A further 100 ml. of the Jones' reagent is added during a further 30 minutes, and sulphuric acid; 230 ml.) is added during 30 minutes to a stirred solution of 1-phenylacetamidopropan-2-ol(146.7 g.) in chloroform (750 ml.) which is maintained below 20° C. A further 100 ml. of the Jones' reagent is added during a further 30 minutes, and the mixture is then diluted with water and the chloroform layer is separated. The aqueous layer is washed with chloroform and the combined chloroform solutions are washed with water, dried over magnesium sulphate and evaporated to dryness under reduced pressure. The solid residue is stirred with ethyl acetate and the mixture is filtered. There is thus obtained as solid product N-(2-oxopropyl)phenylacetamide, m.p. 126° C.

EXAMPLE 12

A mixture of 0.9 g. of 2-(β-aminoethylamino)-1-phenylethanol and 0.9 g. of ethyl phenoxyacetate is heated at 90° C. for 18 hours. The mixture is cooled and the residue is crystallised from isopropanol. There is thus obtained 2-(β-phenoxyacetamidoethyl)amino-1-phenylethanol, m.p. 97°–98° C.

The process described above is repeated except that an appropriate ethyl ester is used in place of ethyl phenoxyacetate. There are thus obtained the compounds described in the following table:

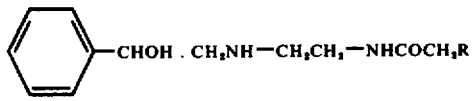

| R | m.p. (° C.) | crystallisation solvent |
|---|---|---|
| p-acetylphenoxy | 124–125 | acetonitrile |
| 3,4-dimethoxyphenyl | 111–112 | ethyl acetate |
| p-cyanophenoxy | 62–63 | aqueous ethanol |
| p-aminophenyl | 132–133 | ethanol |
| o-carbamoylphenoxy | 143–145 | acetonitrile |
| p-acetamidophenyl | 148–149 | water |
| hydroxy | oxalate 160–161 | ethanol |

The process described above is repeated except that ethyl trifluoroacetate is used in place of ethyl phenoxyacetate, and that the product is isolated as an oxalate salt and crystallised from a mixture of acetonitrile and ethanol. There is thus obtained 2-(β-trifluoroacetamidoethyl)amino-1-phenylethanol oxalate, m.p. 186°–187° C.

EXAMPLE 13

A mixture of 2.7 g. of 2-(N-β-aminoethyl-N-benzylamino)-1-phenylethanol, 30 ml. of toluene, 5 ml. of chloroform, 1.5 ml. of triethylamine and 1.58 g. of butyric anhydride is stirred and heated under reflux for 3 hours and then evaporated to dryness. The residue is dissolved in 30 ml. of acetic acid and the solution is shaken with hydrogen in the presence of 0.5 g. of a 30% palladium-on-charcoal catalyst at laboratory temperature and atmospheric pressure until 235 ml. of hydrogen have been absorbed. The mixture is filtered, the filtrate is evaporated to dryness and the residue is stirred with 100 ml. of water. The mixture is basified with aqueous 11N-sodium hydroxide solution and the aqueous solution is saturated with sodium chloride. The mixture is extracted four times with 75 ml. of ethyl acetate each time and the combined ethyl acetate extracts are dried over anhydrous magnesium sulphate and evaporated to dryness under reduced pressure. The residue is crystallised from ethyl acetate and there is thus obtained 2-(β-butyramidoethylamino)-1-phenylethanol, m.p. 90°–91° C.

The process described above is repeated except that 1.86 g. of isovaleric anhydride are used in place of 1.58 g. of butyric anhydride. There is thus obtained 2-(β-isovaleramidoethylamino)-1-phenylethanol, which is characterised as its hydrogen oxalate salt, m.p. 163°–165° C. after crystallisation from acetonitrile.

The 2-(N-β-aminoethyl-N-benzylamino)-1-phenylethanol used as starting material may be obtained as follows:

A solution of 6 g. of styrene oxide in 50 ml. of n-propanol is added to a stirred mixture of 12.8 g. of N-benzyl-N-β-isobutyramidoethylamine, 100 ml. of n-propanol, 4.1 g. of sodium bicarbonate and 10 ml. of water and the mixture is heated at 90° C. for 18 hours and then evaporated to dryness under reduced pressure. The residue is heated for 4 hours at 90° C. with mixture of 100 ml. of aqueous 11N-hydrochloric acid and 100 ml. of water. The mixture is cooled and extracted with 200 ml. of ether, and the aqueous acid phase is basified with aqueous 11N-sodium hydroxide solution and extracted three times with 150 ml. of chloroform each time. The combined chloroform extracts are dried over magnesium sulphate and evaporated to dryness under reduced pressure. The residue is dissolved in 20 ml. of acetonitrile and added to a solution of 12.6 g. of oxalic acid in 100 ml. of acetonitrile. The mixture is filtered and the solid residue is crystallised from ethanol. There is thus obtained 2-(N-β-aminoethyl-N-benzylamino)-1-phenylethanol bisoxalate, m.p. 175°–177° C.

The free base is isolated from the bisoxalate salt by conventional treatment with aqueous base and extraction into chloroform and has m.p. 142°–146° C.

EXAMPLE 14

Triethylamine (4 g.) are added to a stirred solution of 3.69 of α-phenoxypropionyl chloride in 50 ml. of toluene, and a solution of 5.4 g. of 2-(N-β-aminoethyl-N-benxylamino)-1-phenylethanol in 40 ml. of toluene is then added. The mixture is stirred at laboratory temperature for 4 hours and then shaken successively with 30 ml. of water, 20 ml. of aqueous 3N-sodium bicarbonate solution and 20 ml. of water. The toluene phase is separated, dried over anhydrous magnesium sulphate and evaporated to dryness under reduced pressure.

A mixture of 8.3 g. of the residue, 40 ml. of acetic acid and 0.2 g. of a 30% palladium-on-charcoal catalyst is shaken with hydrogen at laboratory temperature and atmospheric pressure until 430 ml. of hydrogen have been absorbed. The mixture is filtered and the filtrate is evaporated to dryness under reduced pressure. A solution of the residue in 30 ml. of ethyl acetate is added to a solution of 2.52 g. of oxalic acid in 20 ml. of ethyl acetate, and the mixture is filtered. The solid residue is triturated with ether and then crystallised from acetonitrile. There is thus obtained 2-β-(α-phenoxypropionamido)ethylamino-1-phenylethanol oxalate, m.p. 107°–108° C.

EXAMPLE 15

A mixture of 1.7 g. of 2-(N-β-aminopropyl-N-benzylamino)-1-phenylethanol, 50 ml. of toluene, 1 ml. of triethylamine and 0.98 g. of phenylacetyl chloride is stirred at laboratory temperature for 30 minutes. The mixture is then washed successively with 20 ml. of aqueous N-sodium hydroxide solution and 20 ml. of water and the toluene phase is separated, dried over anhydrous magnesium sulphate and evaporated to dryness under reduced pressure. A solution of the residue in 30 ml. of ethanol is shaken with hydrogen in the presence of 0.2 g. of a 30% palladium-on-charcoal catalyst at laboratory temperature and atmospheric pressure until 190 ml. of hydrogen have been absorbed. The mixture is filtered and the filtrate is evaporated to dryness under reduced pressure. The residue is triturated with 25 ml. of ether and crystallised from ethylacetate. There is thus obtained 2-β-phenylacetamidopropylamino-1-phenylethanol, m.p. 136°–137° C.

The 2-(N-β-aminopropyl-N-benzylamino)-1-phenylethanol used as starting material may be obtained as follows:

A mixture of 11.35 g. of 2-benzylamino-1-phenylethanol, 100 ml. of acetonitrile, 100 mg. of potassium iodide and 2.32 g. of chloroacetone is heated under reflux for 1½ hours and then filtered. The filtrate is evaporated to dryness under reduced pressure. A mixture of 6.0 g. of the residue, which is 2-(N-benzyl-N-2-oxopropylamino)-1-phenylethanol, 3.0 g. of hydroxylamine hydrochloride, 7.9 potassium carbonate, 50 ml. of ethanol and 10 ml. of water is heated under reflux for 2 hours and then evaporated to dryness under reduced pressure. The residue is diluted with 100 ml of water and extracted three times with 50 ml. of ethyl acetate each time. The combined ethyl acetate extracts are dried over anhydrous magnesium sulphate and evaporated to dryness under reduced pressure.

28.9 Ml. of a 70% w/v solution of sodium bis(2-methoxyethoxy) aluminum hydride in benzene is added during 20 minutes to a stirred solution of 7.0 g. of the residue, which is 2-(N-benzyl-N-2-hydroxyiminopropylamino)-1-phenylethanol, in 100 ml. of toluene and the solution is stirred at laboratory temperature for 18 hours. The mixture is adjusted to pH 2 with aqueous 2N-hydrochloric acid and the toluene phase is separated and extracted with 100 ml. of aqueous 2N-hydrochloric acid. The combined aqueous acidic solutions are basified with aqueous 11N-sodium hydroxide solution and extracted three times with 150 ml. of chloroform each time. The combined chloroform extracts are dried over anhydrous magnesium sulphate and evaporated to dryness under reduced pressure. The residue is dissolved in 50 ml of ether and ethereal hydrogen chloride solution is added. The ethereal phase is decanted off and the residue is crystallised from 15 ml. of a 5:95v/v mixture of methanol and acetonitrile. There is thus obtained 2-(N-β-aminopropyl-N-benzylamino)-1-phenylethanol dihydrochloride, m.p. 197°–198° C. The free base is recovered from the dihydrochloride by conventional means before use.

EXAMPLE 16

Sodium borohydride (0.38 g.) is added to a stirred solution of 1.1 g. of 2-β-(p-acetylphenoxyacetamido)ethylamino-1-phenylethanol (Example 12) in 30 ml. of methanol and the mixture is stirred at a laboratory temperature for 1 hour. The mixture is acidified to pH 3-4 with acetic acid and evaporated to dryness under reduced pressure. The residue is dissolved in 50 ml. of water and the solution is basified with 20 ml. of aqueous 2N-sodium hydroxide solution and then filtered. The solid residue is crystallised from 100 ml. of water and there is thus obtained 2-β-(p-α-hydroxyethylephenoxyacetamido)ethylamino-1-phenylethanol, m.p. 90°–91° C.

Example 17

A mixture of 1.65 of 2-β-(p-benzyloxybenzamido)ethylamino-1-phenylethanol, 50 ml. of acetic acid and 0.3 g. of a 5% palladium-on-charcoal catalyst is shaken with hydrogen at laboratory temperature and atmospheric pressure until 120 ml. of hydrogen have been absorbed. The mixture is filtered and the filtrate is evaporated to dryness under reduced pressure. A solution of the residue in 10 ml. of ethanol is added to a solution of 0.7 g. of oxalic acid in 50 ml. of ethyl acetate, and the mixture is filtered. The solid residue is crystallised from ethanol and there is thus obtained 2-β-(p-hydroxybenzamido)ethylamino-1phenylethanol oxalate, m.p. 185°–186° C.

The 2-β-(p-benzyloxybenzamido)ethylamino-1-phenylethanol used as starting material may be obtained as follows:

A mixture of 2.7 g. of N-(β-aminoethyl)-p-benzyloxybenzamide, 1.2 g. of styrene oxide and 50 ml. of isopropanol is heated under reflux for 18 hours. The mixture is evaporated to dryness under reduced pressure and the residue is crystallised from ethyl acetate. There is thus obtained 2-β-(p-benzyloxybenzamido)ethylamino-1-phenylethanol, m.p. 150°–151° C.

EXAMPLE 18

Phenylacetyl chloride 1.20 ml. is added dropwise to a cooled, stirred solution of 2-(2-amino-1-methylethyl)-amino-1-phenylethanol (1.74 g.; Example 22 a or b) in tetrahydrofuran (50 ml.) and the mixture is stirred for 10 minutes and then evaporated to dryness under reduced pressure. The residue is partitioned between 50 ml. of ether and 50 ml. of aqueous 2N-hydrochloric acid and the aqueous acidic layer is separated and basified to pH 10 with potassium carbonate. The mixture is extracted three times with chloroform (25 ml. each time) and the combined extracts are washed with saturated brine, dried over anhydrous sodium sulphate and evaporated to dryness under reduced pressure. A solution of the residue in 20 ml. of hot ethyl acetate is added to a solution of oxalic acid dihydrate (1.26 g.) in 15 ml. of hot ethanol and the mixture is cooled at −20° C. for 18 hours and then filtered. The solid residue if formed is discarded and the filtrate is evaporated to dryness. The residue is crystallised from ethanol and there is thus obtained 2-(1-methyl-2-phenylacetamidoethyl)amino-1-phenylethanol hydrogen oxalate, m.p. 160°–161° C.

EXAMPLE 19

The compound 2-(1-methyl-2phenylacetamidoethyl)amino-1-phenylethanol has two asymmetric centres and when obtained by the process described in Example 4, 10, 11 or 18 is a mixture of two racemic diastereoisomeric forms. These forms may be separated one from the other as follows:

A mixture of 3.8 g. of 2-(1-methyl-2-phenylacetamidoethyl)amino-1-phenylethanol hydrogen oxalate (m.p. 160°–161° C.; Example 4) is stirred with 50 ml. of 10% aqueous potassium carbonate solution and 50 ml. of ethyl acetate. The ethyl acetate phase is separated, dried over anhydrous magnesium sulphate, and evaporated to dryness under reduced pressure. The residue is crystallised four times from 20 ml. of toluene each time. There is thus obtained one specific diastereoisomer (Isomer A) of 2-(1-methyl-2-phenylacetamidoethyl)amino-1-phenylethanol, m.p. 100°–101° C.

The mother liquors from the first toluene crystallisation are evaporated to dryness under reduced pressure and the residue is crystallised twice from 20 ml. of a 1:3 v/v mixture of ethyl acetate and cyclohexane. There is thus obtained a second specific diastereoisomer (Isomer B) of 2-(1-methyl-2-phenylacetamidoethyl)amino-1-phenylethanol, m.p. 96°–98° C.

Isomer A is characterised by the proton magnetic resonance spectrum of the carbon-attached proton of the -CHOH- group, which is a triplet at $\delta$= approximately 4.5. This compound is a racemic mixture of the enantiomer in which both asymmetric centres have the (R)— configuration and the enantiomer in which both asymmetric centres have the (S)— configuration.

Isomer B is similarly characterised by the spectrum of the carbon-attached proton of the -CHOH- group, which is quartet at $\beta$= approximately 4.5. This compound is a racemic mixture of enantiomers in which the two asymmetric centres have opposite absolute configurations, that is, a mixture of (R), (S) and (S), (R) forms.

EXAMPLE 20

The process described in Example 18 is repeated except that (1R)-2-[(1S) -2-amino-1-methylethyl]amino-1-phenylethanol (Example 22 c) is used as starting material. There is thus obtained (1R)-2-[(1S)-1-methyl-2-phenylacetamidoethyl]-amino-1-phenylethanol hydrogen oxalate, m.p. 138°–140° C., $[\alpha]_D$=−18.5° C. (C=2, aqueous N-hydrochloric acid). The proton magnetic resonance spectrum shows a quartet at $\delta$= approximately 4.5.

EXAMPLE 21

The process described in Example 18 is repeated except that (1R) -2-[(1R)-1-amino-1-methylethyl]amino-1-phenylethanol (Example 22 d) is used as starting material. There is thus obtained (1R)-2-[(1R)-1-methyl-2-phenylacetamidoethyl]-amino-1-phenylethanol hydrogen oxalate, m.p. 155°–159° C., $[\alpha]_D$=−33.2° C. (C=2, aqueous N-hydrochloric acid). The proton magnetic resonance spectrum shows a triplet at $\delta$= approximately 4.5.

EXAMPLE 22

The novel compound 2-(2-amino-1-methylethyl)amino-1-phenylethanol, used as an intermediate in EXAMPLE 17 and 19, may be obtained in various ways, as follows:

a. A solution of 1-nitropropan-2-one (12.5 g.) in ethanol (100 ml.) is added to a solution of 2-amino-1-phenylethanol (13.7 g.) in ethanol (100 ml.) and the mixture is stirred at laboratory temperature for 1 hour and then filtered. The filtrate is evaporated to dryness under reduced pressure and the residue is dissolved in a 1:3 v/v mixture of methanol and chloroform and passed through a silica gel chromatography column which is eluted with more of the same solvent mixture. The eluate is evaporated to dryness and the residue is crystallised from chloroform. There is thus obtained 2-(1-methyl-2-nitrovinyl)amino-1-phenylethanol, m.p. 124°–125° C.

The above compound (2.22 g.) is added under an atmosphere of nitrogen to a stirred suspension of a nickel boride catalyst (prepared as described in the Journal of Organic Chemistry, 1971, 36, 2018 from 1.18 g. of nickel chloride and 0.19 g. of sodium borohydride) in 95% v/v aqueous ethanol which is maintained by cooling at laboratory temperature, and sodium borohydride (0.76 g.) is then added portionwise during 30 minutes. The catalyst is removed by centrifugation and the solution is evaporated to dryness. The residue is extracted twice with methylene chloride (75 ml. each time) and the combined extracts are dried over sodium sulphate and evaporated to dryness under reduced pressure. The residue consists of 2-(2-amino-1-methylethyl)amino-1-phenylethanol.

b. Acetaldehyde cyanohydrin (10.65 g.) is added to a solution of 2-amino-1-phenylethanol (13.7 g.) in tetrahydrofuran (100 ml.) and the mixture is kept at laboratory temperature for 18 hours and then evaporated to dryness under reduced pressure. The residue is crystallised from toluene and there is thus obtained 2-α-cyanoethylamino-1-phenylethanol, m.p. 96°–98° C. A solution of 4.75 g. of the above compound in tetrahydrofuran (40 ml.) is added during 1 hour under an atmosphere of nitrogen to a stirred suspension of lithium aluminium hydride (0.95 g.) in tetrahydrofuran (30 ml.) and the mixture is stirred for a further 1 hour. Water (1 ml.), aqueous 15% potassium hydroxide solution (1 ml.) and water (3 ml.) are successively and cautiously added, and the mixture is filtered. The solid is washed with tetrahydrofuran and the combined filtrate and washings are dried over sodium sulphate and evaporated to dryness under reduced pressure. The residue consists of 2-(2-amino-1-methylethyl)amino-1-phenylethanol.

c. 1-Hydroxybenzotriazole (7.4 g.), (S)-(+)-alaninamide (5.1 g.) and dicyclohexylcarbodiimide (11.3 g.) are successively added to a stirred solution of (R)-(−)-mandelic acid (7.6 g.) in N,N-dimethylformamide (150 ml.) and the mixture is stirred at laboratory temperature for 17 hours. Glacial acetic acid (3 ml.) is added, the mixture is filtered and the solid is washed with N,N-dimethylformamide. The combined filtrate and washings are evaporated to dryness under reduced pressure at a temperature not greater than 45° C. The residue is dissolved in ethyl acetate (800 ml.) and the solution is washed four times with a 1:1 v/v mixture of saturated brine and saturated aqueous sodium bicarbonate solution (75 ml. each time) and then dried and evaporated to dryness under reduced pressure.

A molar solution of borane-tetrahydrofuran complex in tetrahydrofuran (182 ml.) is cautiously added to a solution of the residue (8.6 g.) in tetrahydrofuran (80 ml.) which is maintained at 5° C., and the mixture is then kept at laboratory temperature for 18 hours. Water is cautiously added dropwise until the excess of diborane is destroyed and the mixture is evaporated to dryness under reduced pressure. The residue is dissolved in aqueous 2N-hydrochloric acid (100 ml.) and the solution is washed three times with ether (100 ml. each time), made alkaline with aqueous sodium hydroxide solution and saturated with sodium potassium tartrate. The mixture is extracted three times with a 9:1 v/v mixture of methylene chloride and ether (100 ml. each time) and the combined extracts are dried and evaporated to dryness under reduced pressure.

The residue is dissolved in tetrahydrofuran (40 ml.) and the borane-tetrahydrofuran reduction described above is repeated using 93 ml. of molar reagent. The residue isolated as described above is dissolved in aqueous 6N-hydrochloric acid (60 ml.) and the solution is heated at 90° C. for 10 minutes, diluted with water (20 ml.) and cooled, and then washed with ether and basified and the product is extracted into methylene chloride/ether as described above. There is thus obtained, as a pale yellow oil, (1R)-2-[(1S)-2-amino-1-methylethyl]amino-1-phenylethanol.

d. The process described in part (c) above is repeated except that (R)-(−)-alaninamide is used in place of (S)-(+)-alaninamide. There is similarly obtained, again as a pale yellow oil, (1R)-2-[(1R)-2-amino-1-methylethyl]amino-1-phenylethanol.

EXAMPLE 23

A mixture of 2-β-aminoethylamino-1-phenylethanol (1.0 g.), ethyl chloroformate (1.09 g.), potassium carbonate (1.38 g.) and ethanol (40 ml.) is heated under reflux for 30 minutes, cooled and evaporated to dryness. The residue is dissolved in aqueous N-hydrochloric acid (30 ml.) and the solution is washed with ethyl acetate and then basified with sodium bicarbonate. The mixture is extracted three times with ethyl acetate and the combined extracts are dried and evaporated to dryness. The residue is crystallised from a mixture of ethyl acetate and petroleum ether (b.p. 60°–80° C.) and there is thus obtained 2-(β-ethoxycarbonamidoethyl)amino-1-phenylethanol, m.p. 90°–91° C.

What we claim is:

1. An ethanolamine derivative selected from the group consisting of a compound of the formula:

wherein A is alkylene of from 2 to 6 carbon atoms, wherein $R^1$ is hydrogen or alkyl, alkenyl, halogenoalkyl or cycloalkyl each of up to 6 carbon atoms, or aryl of the formula:

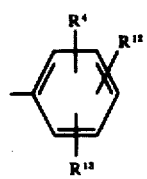

wherein $R^2$, $R^3$, $R^{12}$ and $R^{13}$, which may be the same or different, each is hydrogen, halogen, nitro, amino or cyano, or alkyl alkenyl, alkoxy, alkenyloxy, hydroxyalkyl, alkanoyl, acylamino or alkanesulphonamido each of up to 6 carbon atoms, wherein $R^4$ is hydrogen, hydroxy or carbamoyl, wherein $R^5$ is hydrogen or alkyl of up to 6 carbon atoms, wherein X is sulphonyl and wherein Y is a direct link, or alkylene or alkylenoxy each of up to 6 carbon atoms, or imino (—NH—) or (except when $R^1$ is hydrogen) oxygen; and an acid-addition salt thereof.

2. An ethanolamine derivative as claimed in claim 1 selected from the group consisting of a compound of the formula given in claim 1 wherein A is ethylene, 1-methylethylene or 1,1-dimethylethylene, wherein $R^1$ is alkyl or cycloalkyl each of up to 6 carbon atoms, wherein $R^2$ and $R^3$ are both hydrogen, and wherein Y is a direct link, and an acid-addition salt thereof.

3. An ethanolamine derivative as claimed in claim 1 selected from the group consisting of a compound of the formula given in claim 1 wherein A is ethylene, 1-methylethylene or 1,1-dimethylethylene, wherein $R^1$ is phenyl, chlorophenyl or methoxyphenyl, wherein $R^2$ and $R^3$ are both hydrogen, and wherein Y is methylene, and an acid-addition salt thereof.

4. An ethanolamine derivative as claimed in claim 1 selected from
 1-phenyl-2-(β-benzenesulphonamidoethyl)aminoethanol; or an acid-addition salt thereof.

5. An ethanolamine derivative as claimed in claim 1 selected from
 1-phenyl-2-(β-n-propanesulphonamidoethyl)aminoethanol or an acid-addition salt thereof.

6. An ethanolamine derivative as claimed in claim 1 selected from
 1-phenyl-2-(β-benzylsulphonamidoethyl)aminoethanol or an acid-addition salt thereof.

7. An ethanolamine derivative as claimed in claim 1 selected from
1-phenyl-2-(β-o-nitrobenzenesulphonamidoethyl-)aminoethanol or an acid-addition salt thereof.

8. An acid-addition salt as claimed in claim 1 which is a hydrochloride, hydrobromide, phosphate, sulphate, oxalate, lactate, tartrate, acetate, salicylate, citrate, benzoate, β-naphthoate, adipate or 1,1-methylene-bis-(2-hydroxy-3-napthoate), or a salt derived from a sulphonated polystyrene resin.

9. A pharmaceutical composition having β-adrenergic blocking activity, comprising as active ingredient an effective amount of at least one alkanolamine derivative or an acid-addition salt thereof, claimed in claim 1, in association with a pharmaceutically-acceptable carrier therefor.

10. A method for the treatment or prophylaxis or angina pectoris and cardiac arrhythmias and hypertension in warm-blooded animals which comprises administering to said animals an effective amount of at least one compound claimed in claim 1.

11. A method of producing coronary β-adrenergic blockade in warm-blooded animals in need of such blockade which comprises administering to said animals an effective amount of at least one compound claimed in claim 1.

* * * * *